(12) United States Patent
Geppert et al.

(10) Patent No.: US 9,707,319 B2
(45) Date of Patent: Jul. 18, 2017

(54) DEVICE AND METHOD FOR IMPROVING HYDRATION OF A BIOMATERIAL

(71) Applicant: Nordson Corporation, Westlake, OH (US)

(72) Inventors: Kevin C. Geppert, Eagan, MN (US); Thomas A. Kirk, Hastings, MN (US)

(73) Assignee: Nordson Corporation, Westlake, OH (US)

( * ) Notice: Subject to any disclaimer, the term of this patent is extended or adjusted under 35 U.S.C. 154(b) by 209 days.

(21) Appl. No.: 14/306,852

(22) Filed: Jun. 17, 2014

(65) Prior Publication Data
US 2014/0373922 A1 Dec. 25, 2014

Related U.S. Application Data

(60) Provisional application No. 61/837,315, filed on Jun. 20, 2013.

(51) Int. Cl.
*F17D 1/20* (2006.01)
*A61L 27/50* (2006.01)
(Continued)

(52) U.S. Cl.
CPC .......... *A61L 27/50* (2013.01); *A61B 17/8825* (2013.01); *A61B 17/8827* (2013.01);
(Continued)

(58) Field of Classification Search
CPC ...... B01F 13/0023; A61B 2017/11495; A61M 5/19; A61M 5/2448; A61M 2005/3132; A61L 27/50
(Continued)

(56) References Cited

U.S. PATENT DOCUMENTS 3,437,242 A * 4/1969 Poitras ............... B65D 81/3255
222/129
3,859,999 A * 1/1975 Ishikawa ............... A61M 5/178
604/190
(Continued)

FOREIGN PATENT DOCUMENTS

DE 102005030510 A1 1/2007
EP 0148116 A1 7/1985
(Continued)

OTHER PUBLICATIONS

European Patent Office, International Search Report and Written Opinion in PCT Application Serial No. PCT/US14/042913, Oct. 1, 2014.

*Primary Examiner* — Reinaldo Sanchez-Medina
(74) *Attorney, Agent, or Firm* — Baker & Hostetler LLP

(57) ABSTRACT

A device and method for improving hydration of a biomaterial includes a syringe having a cavity therein and a distal opening, an end cap, and a wall operatively coupled to the end cap. The end cap has a distal plate with an inlet and is removably attached to the syringe to cover the distal opening. The wall is positioned proximate to the inlet and at least partially defines a volume in fluid communication with the inlet. An orifice extends through the wall and fluidly connects the volume to the cavity. A flow of a liquid component of biomaterial diffuses through the orifice and is introduced into a particulate component of biomaterial. As such, the liquid component of biomaterial hydrates the particulate component of biomaterial.

27 Claims, 5 Drawing Sheets

(51) Int. Cl.
| | |
|---|---|
| *A61F 2/28* | (2006.01) |
| *A61F 2/46* | (2006.01) |
| *B01F 5/06* | (2006.01) |
| *B01F 13/00* | (2006.01) |
| *B01F 15/02* | (2006.01) |
| *B01F 3/12* | (2006.01) |
| *A61B 17/88* | (2006.01) |

(52) U.S. Cl.
CPC .............. *A61F 2/28* (2013.01); *A61F 2/4601* (2013.01); *B01F 3/1228* (2013.01); *B01F 5/0688* (2013.01); *B01F 5/0693* (2013.01); *B01F 13/0023* (2013.01); *B01F 15/0225* (2013.01); *A61B 2017/8838* (2013.01); *A61F 2002/2835* (2013.01); *B01F 2003/1257* (2013.01); *Y10T 137/0318* (2015.04); *Y10T 137/87265* (2015.04); *Y10T 137/87281* (2015.04)

(58) Field of Classification Search
USPC ....... 137/109, 110, 206, 601.19; 604/82, 85, 604/89, 185, 187, 191
See application file for complete search history.

(56) References Cited

U.S. PATENT DOCUMENTS

| | | | | | |
|---|---|---|---|---|---|
| 4,735,509 | A | * | 4/1988 | Rausch | B01F 11/0054 222/129 |
| 4,859,336 | A | * | 8/1989 | Savas | B01D 29/05 210/416.1 |
| 5,254,093 | A | * | 10/1993 | Bartlett | A61M 5/5013 604/110 |
| 5,264,184 | A | * | 11/1993 | Aysta | B01D 61/18 210/473 |
| 5,501,371 | A | * | 3/1996 | Schwartz-Feldman | A61C 9/0026 222/136 |
| 2001/0016703 | A1 | | 8/2001 | Wironen et al. | |
| 2001/0047187 | A1 | * | 11/2001 | Milo | A61B 17/0057 606/213 |
| 2002/0045865 | A1 | * | 4/2002 | Mitomi | A61M 5/3134 604/207 |
| 2002/0052579 | A1 | * | 5/2002 | Sogaro | A45D 19/02 604/218 |
| 2004/0138611 | A1 | * | 7/2004 | Griffiths | A61M 5/2033 604/82 |
| 2005/0209555 | A1 | | 9/2005 | Middleton et al. | |
| 2007/0112308 | A1 | * | 5/2007 | Kay | B01F 3/04446 604/187 |
| 2010/0082013 | A1 | * | 4/2010 | Braga | A61M 5/31596 604/518 |
| 2010/0106138 | A1 | * | 4/2010 | Chavarria | A61B 17/00491 604/518 |
| 2010/0298811 | A1 | * | 11/2010 | Connair | A61M 5/002 604/518 |
| 2011/0060361 | A1 | | 3/2011 | Schweiss et al. | |

FOREIGN PATENT DOCUMENTS

| | | |
|---|---|---|
| EP | 1338332 A1 | 8/2003 |
| FR | 2914566 A1 | 10/2008 |
| WO | 9857734 A1 | 12/1998 |
| WO | 0049319 A1 | 8/2000 |
| WO | 2007084919 A1 | 7/2007 |
| WO | 2013063451 A1 | 5/2013 |

\* cited by examiner

DEVICE AND METHOD FOR IMPROVING HYDRATION OF A BIOMATERIAL

CROSS-REFERENCE TO RELATED APPLICATION

This application claims the benefit of Application Ser. No. 61/837,315 filed Jun. 20, 2013, the disclosure of which is hereby incorporated by reference herein.

TECHNICAL FIELD

The present invention relates generally to devices and methods for hydration of biomaterials, and more particularly, to a devices and methods for hydration of a particulate component of bone graft biomaterial with a liquid component of bone graft material.

BACKGROUND

Bone grafting is a surgical procedure for repairing bones and typically involves introducing a mixture of material components, such as bone graft material, into an area of bone that requires repair, such as a fracture. The bone graft material is intended to stimulate growth of healthy native bone tissue, and new native bone tissue may eventually replace the bone graft material completely. Bone graft material is a type of biomaterial and typically includes a combination of crushed bone, or other particulate component, and a liquid component, such as blood, plasma, or growth factors. Bone graft materials can be allograft (derived from a human other than the one receiving the graft), autograft (derived from the human receiving the graft), and synthetic (created from, for example, ceramics like calcium phosphates).

Bone graft materials are typically delivered to a surgical site using syringe-like delivery devices, which often include attachments, such as small diameter cannulae. The bone graft materials may also be mixed within the delivery device. The liquid component is introduced into the particulate component already contained within the syringe and effectively "hydrates" the particulate component. However, the time and ability of the liquid component to effectively hydrate the particulate component depends, at least in part, on the size of the particulate used in the surgical procedure.

For example, particulate components of bone graft material may vary in size from relatively course particulates to relatively fine, powder-like particulates. On one hand, the liquid component tends to distribute more effectively throughout the relatively course particulate of biomaterial contained within the syringe. On the other hand, relatively fine, powder-like particulates tend to retain greater concentrations of the liquid component in localized concentrations of the particulate. Such localized concentrations of the liquid component may fail to distribute effectively throughout the particulate component resulting in additional surgical time and, in turn, a reduced likelihood of favorable patient outcomes.

There is a need for a device and method for improving hydration of biomaterials, such as a mixture of bone graft materials, that effectively hydrates a particulate component of a biomaterial while addressing issues such as those discussed above.

SUMMARY

An exemplary embodiment of a device for improving hydration of a particulate component of biomaterial with a liquid component of biomaterial includes a syringe, a distal plate, and a wall operatively coupled to the distal plate. The syringe has a syringe body and a cavity therein for containing the particulate component. The syringe body includes a distal opening. The distal plate is operatively connected to the syringe body and at least partially covers the distal opening. In addition, an inlet extends through the distal plate for receiving the liquid component. The wall is positioned proximate to the inlet and at least partially defines a volume in fluid communication with the inlet. The wall is also configured to maintain the volume between the inlet and the particulate component within the cavity of the syringe. Furthermore, at least one orifice extends through the wall and fluidly connects the volume to the cavity. The cross-sectional area of the orifice is less than the cross-sectional area of the inlet. As such, the liquid component received by the inlet flows throughout the volume. The liquid component also flows into the cavity via the orifice for diffusion of the liquid component and hydration of the particulate component within the cavity of the syringe.

According to another exemplary embodiment, a diffuser for improving hydration of the particulate component of biomaterial with a liquid component of biomaterial includes a wall connected to a distal plate. The distal plate has an inlet extending therethrough and is configured for operative attachment to a syringe. Furthermore, at least one orifice extends through the wall. The wall is positioned proximate to the inlet and at least partially defines a volume in fluid communication with the inlet. The cross-sectional area of the orifice is less than the cross-sectional area of the inlet. As such, the liquid component received by the inlet flows throughout the volume and through the orifice for diffusion of the liquid component and hydration of the particulate component within the cavity of the syringe.

In use, a flow of the liquid component of biomaterial is diffused through at least one orifice in a wall in order to form at least one diffused flow of liquid component. The method also includes introducing the diffused flow of the liquid component into a particulate component within a syringe. In addition, the method includes distributing the liquid component throughout the particulate component in order to hydrate the particulate component of biomaterial with the liquid component of biomaterial.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
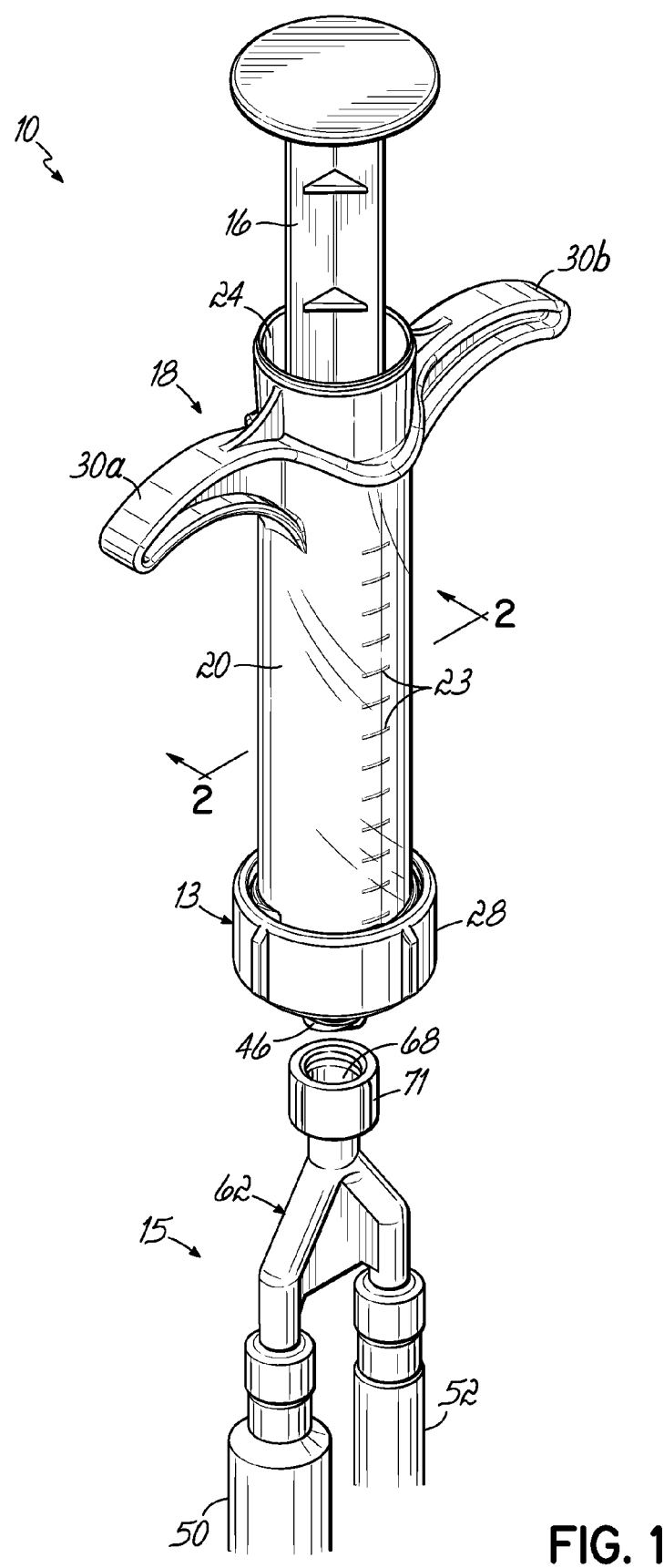
FIG. 1 is a disassembled perspective view of a first embodiment of a device for improving hydration of a particulate component of bone graft material with a liquid component of bone graft material.
Figure 2:
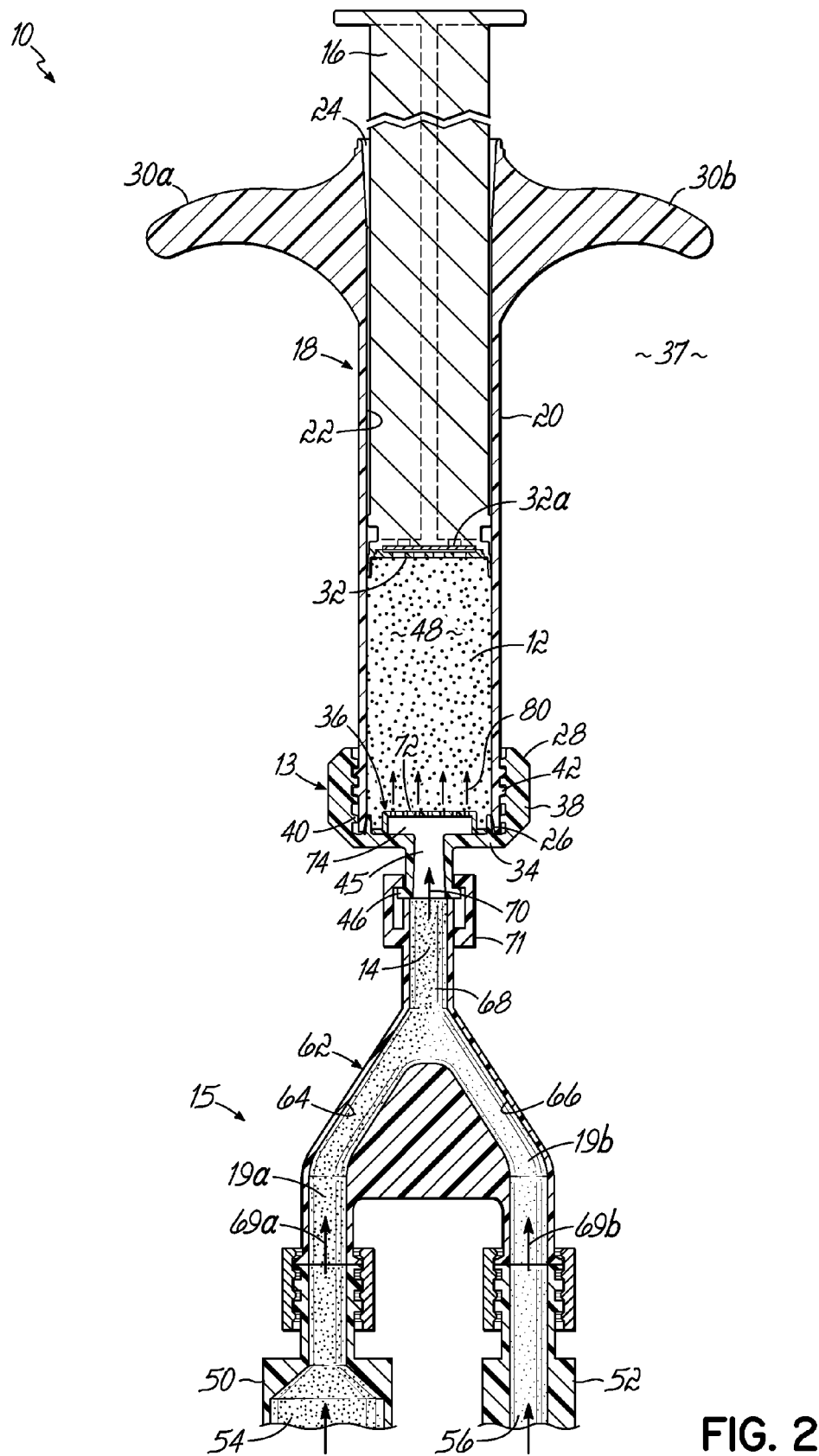
FIG. 2 is a cross-sectional view taken along section line 2-2 of FIG. 1 but showing the device assembled.

With reference to FIG. 1 and FIG. 2, an embodiment of a device 10 for improving hydration of a particulate component 12 of biomaterial with a liquid component 14 of biomaterial includes a plunger 16 positioned within a syringe 18. The particulate component 12 is contained within the syringe 18 against a diffuser 13, whereas the liquid component 14 is initially contained within a fluid source syringe 15. The fluid source syringe 15 fluidly connects to the diffuser 13 for diffusing and distributing the liquid component 14 in order to improve hydration of the particulate component 12 with the liquid component 14 and, in turn, form a mixture of biomaterials. However, the device 10 may be fluidly connected to any source of the liquid component 14 for receiving the liquid component 14. According to an exemplary embodiment, the particulate component 12 is a relatively dry particulate bone graft material, and the liquid component 14 includes a combination of first and second liquid bone graft materials 19a, 19b. However, it will be appreciated that the mixture of biomaterials may be any combination of biomaterial components, such as one or more particulate components and one or more liquid components. It will be further appreciated that the invention described herein may be used with any type of biomaterial. For example, the mixture of biomaterials may be comprised of liquid and particulate components of cartilage materials.

The syringe 18 has a generally cylindrical syringe body 20 with a cavity 22 extending longitudinally therethrough. The cavity 22 within the syringe body 20 extends from a proximal opening 24 to a distal opening 26 of the syringe 18. A plurality of indices 23 are positioned longitudinally along the syringe body 20 for indicating an amount of biomaterial contained within the cavity 22. With respect to the use of the terms "distal" and "proximal," it will be appreciated that such directions and/or locations are intended to describe relative locations longitudinally along exemplary embodiments of the device 10. Similarly, a generally longitudinal direction extends along a length of the device 10 in either a distal or proximal direction. And a transverse direction extends generally orthogonal to or across the longitudinal direction at any angle. It is not intended that these terms or any other spatial references limit the invention to any of the exemplary embodiments described herein.

The distal opening 26 is covered by the diffuser 13, which includes an end cap 28 removably attached to the syringe body 20 for fluidly communicating the first and second liquid bone graft materials 19a, 19b from the fluid source syringe 15 to the cavity 22 within the syringe 18. Ultimately, the proximal opening 24 receives the plunger 16 for insertion into the cavity 22 as shown in FIGS. 1 and 2. In this respect, the plunger 16 is removably inserted within the cavity 22 for longitudinal translation along the syringe body 20 in both the proximal and distal directions. The syringe 18 also includes a pair of finger grips 30a, 30b projecting outwardly from the syringe body 20 away from the cavity 22 for providing additional grip to manipulate the plunger 16 relative to the syringe body 20 during a medical procedure. Such medical procedures for use with the device 10 may include, but are not limited to, bone grafting, cartilage replacement, or any other medical procedure requiring hydration of a biomaterial component. Generally, the manipulation of the device 10 may be performed by a practitioner, such as a doctor, nurse, or similarly trained medical professional.

Prior to receiving the removable plunger 16 as shown in FIG. 1 and FIG. 2, the proximal opening 24 receives the particulate component 12 for placement within cavity 22 toward the distal opening 26. As shown in an exemplary embodiment, the syringe body 20 is tapered at the proximal opening 24 for receiving a funnel (not shown) in fluid communication with the cavity 22 that aids in directing the particulate component 12 into the cavity 22. Once the plunger 16 is inserted into the cavity 22, a stopper end 32 of the plunger 16 compacts the particulate component 12 toward an inner face 33 (see FIG. 3) of a distal plate 34, which at least partially cover the distal opening 26. According to an exemplary embodiment, at least a portion of the distal plate 34 forms the end cap 28. More particularly, the stopper end 32 compacts the particulate component 12 against a first embodiment of a wall 36 of the diffuser 13 configured for diffusing and distributing the liquid component 14 throughout the particulate component 12.

An exemplary embodiment of the stopper end 32 also includes a filter media 32a for venting gas, such as air, from the cavity 22 to an exterior environment 37. The filter media 32a is configured for allowing gas to pass therethrough and move proximally beyond the stopper end 32, but inhibit proximal movement of the particulate component 12. Accordingly, the stopper end may compact the particulate component in the cavity 22, while venting gas proximally along the plunger 16, through the proximal opening 24, and into the exterior environment 37.

Figure 3:
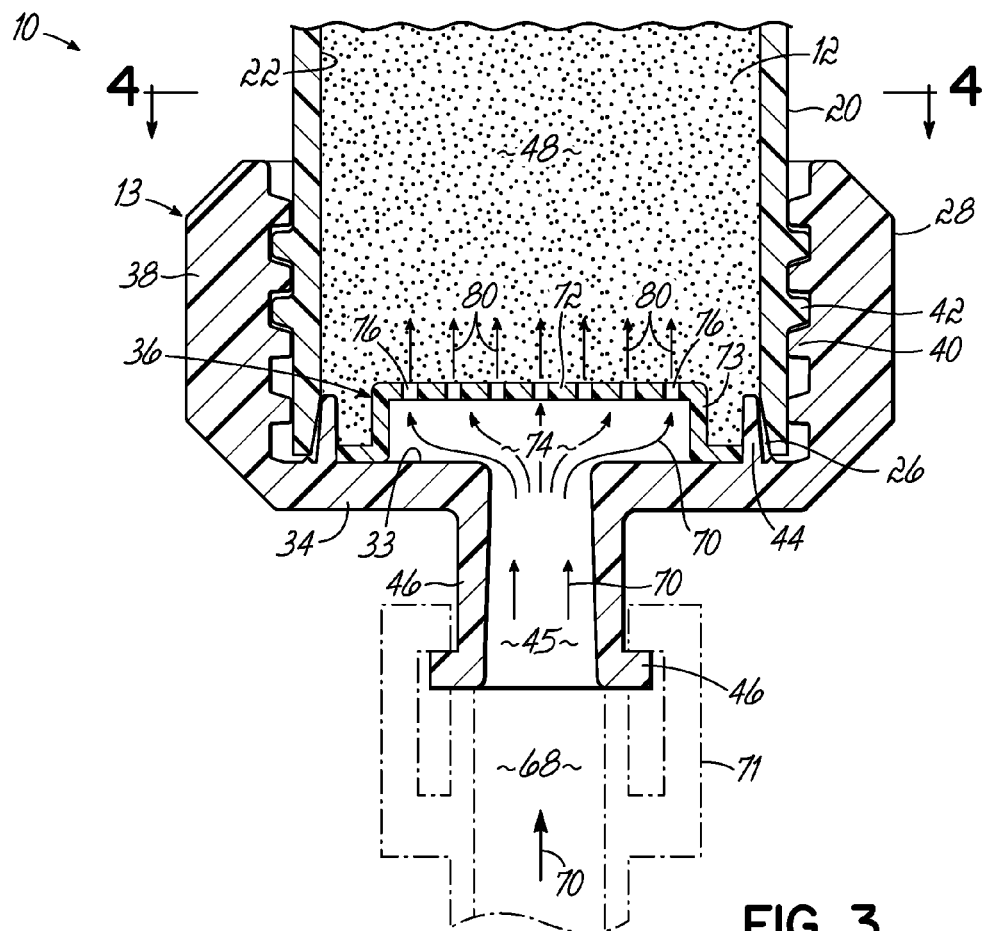
FIG. 3 is an enlarged cross-sectional view of FIG. 2 showing a diffuser with a wall including a baffle plate.

As best shown in FIG. 2 and FIG. 3, the end cap 28 also includes an annular wall 38 having an inner screw thread 40 that rotates onto an outer screw thread 42 of the syringe body 20 for removably fastening the end cap 28 to the syringe body 20. The distal plate 34 is generally orthogonal to the annular wall 38 and extends therebetween. The distal plate includes an inner annular lip 44 and a coupling for connecting to the fluid source syringe 15. According to an exemplary embodiment, the coupling is in the form of a male luer coupling 46 projecting distally from the remainder of the end cap 28 having an inlet 45 extending therethrough.

As the end cap 28 tightens onto the syringe body 20, the inner annular lip 44 engages the syringe body 20 adjacent to the distal opening 26 and fluidly seals the end cap 28 to the syringe body 20. Similarly, the stopper end 32 of the plunger 16 annularly seals against the syringe body 20 for inhibiting the particulate component 12 and the liquid component 14 from moving proximally past the stopper end 32. As such, the syringe body 20, the distal plate 34, the wall 36, and the stopper end 32 collectively define a chamber 48 for containing the particulate and liquid components 12, 14 of biomaterials once received therein. According to the exemplary embodiment, the chamber 48 is configured to receive approximately 15 cc of the biomaterial components. However, it will be appreciated that the device 10 may also be configured for receiving any volume of biomaterial components desirable for use by the practitioner in accordance with the principles of the invention described herein.

An exemplary embodiment of the fluid source syringe 15 includes first and second syringe housings 50, 52 that each respectively define first and second syringe chambers 54, 56. The first and second syringe chambers 54, 56 each contain respective first and second liquid bone graft materials 19a, 19b. Furthermore, the fluid source syringe 15 includes an adapter 62, which defines a first channel 64 and a second channel 66 that join together into a primary channel 68. The first and second liquid bone graft materials 19a, 19b similarly flow from the first and second syringe chambers 54, 56, as indicated by arrows 69a, 69b, and flow together in the primary channel 68 to form the liquid component 14 of biomaterial, indicate by arrows 70. As such, the first and second channels 64, 66 are fluidly connected to the first and second syringe chambers 54, 56 and the primary channel 68 is configured for fluid attachment to the end cap 28. More particularly, the primary channel 68 extends through a female luer coupling 71, which connects to the male luer coupling 46. In turn, the primary channel 68 fluidly communicates the liquid component 14 to the inlet 45.

Figure 4:
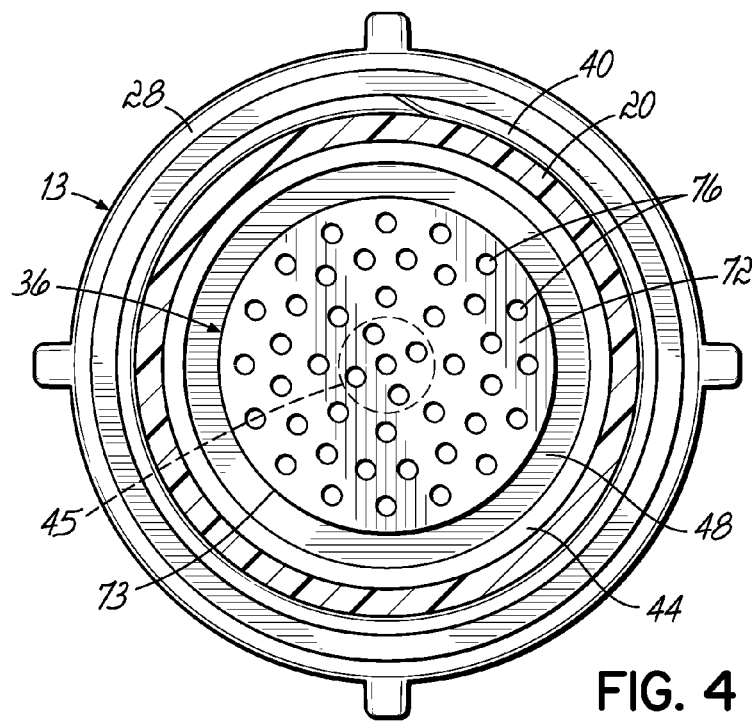
FIG. 4 is a cross-sectional view taken along section line 4-4 of FIG. 3.

With respect to FIG. 3 and FIG. 4, the first embodiment of the wall 36 includes a baffle plate 72 and an annular sidewall 73. The baffle plate 72 is generally circular and positioned offset and generally parallel to the distal plate 34. The annular sidewall 73 extends distally from the baffle plate 72 to the distal plate 34 where the annular sidewall 73 connects to the distal plate 34. In this respect, a circumference of the baffle plate 72 is generally larger than a circumference of the inlet 45. According to an exemplary embodiment, wall 36 is of unitary construction.

The baffle plate 72, the annular sidewall 73, and the distal plate 34 define a volume 74 in fluid communication with the inlet 45. In this respect, the wall 36 maintains the volume 74 between the inlet 45 and the particulate component 12. Furthermore, a plurality of orifices 76 extend in a generally longitudinal direction through the baffle plate 72 for fluidly connecting the volume 74 to the chamber 48. The plurality of orifices 76 operatively diffuse the liquid component 14 and allow the liquid component 14 to pass through the baffle plate 72 for uniformly hydrating the particulate component 12 generally throughout the cross-sectional area of the chamber 48 and then along its length in a proximal direction. In the alternative, rather than the plurality of orifices 76, the baffle plate 72 may include as few as one orifice configured for diffusing the liquid component 14. For example, the orifice may be formed in the shape of an "X" or "+" or other configuration for diffusing the liquid component 14.

According to an exemplary embodiment of the baffle plate 72, the plurality of orifices 76 are radially arranged about the baffle plate 72 in generally circular rows. More particularly, the plurality of orifices 76 includes one centrally positioned orifice 76 and four generally circular rows of orifices 76. The first, second, third, and fourth generally circular rows of orifices 76 respectively include four, eight, sixteen, and sixteen orifices generally evenly distributed about the baffle plate 72. As such, an exemplary embodiment of the baffle plate 72 includes forty-five orifices 76, each of which extends generally longitudinally through the baffle plate 72 and generally parallel to the inlet 45. However, it will be appreciated that any number of orifices 76 may be similarly used and vary in shape and size. As such, the baffle plate 72 is not intended to be limited to the exemplary embodiments described herein.

Furthermore, each of the orifices 76 has an individual cross-sectional area through which the liquid component 14 may flow from the volume 74 to the chamber 48. In order to encourage a generally equal flow 70 of the liquid component 14 through each of the orifices 76, the plurality of orifices 76 are sized such that the baffle plate 72 generates a back pressure against the flow 70 of liquid component 14. In this respect, the individual cross-sectional areas of the plurality of orifices 76 aggregates to a cumulative cross-sectional area, whereas the inlet 45 has an inlet cross-sectional area. According to an exemplary embodiment in which the baffle plate 72 generates back pressure, the cumulative cross-sectional area of the orifices 76 is less than the inlet cross-sectional area. However, it will be appreciated that the diffuser 13 may alternatively diffuse the liquid component 14 without the presence of back pressure. Thus, the invention described herein is not intended to necessarily be limited to include the plurality of orifices 76 with the cumulative cross-sectional area less than the inlet cross-sectional area.

Figure 5:
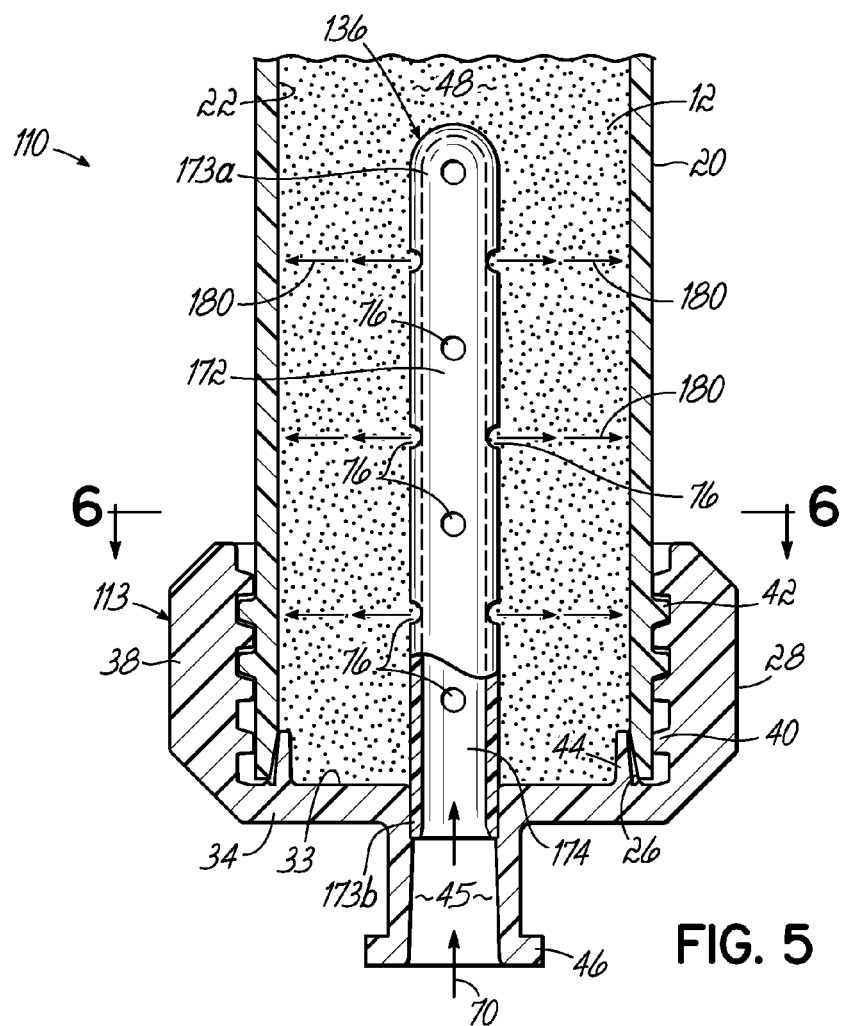
FIG. 5 is an enlarged cross-sectional view similar to FIG. 3, but showing a second embodiment of a device having a diffuser with a wall including a cannula.
Figure 6:
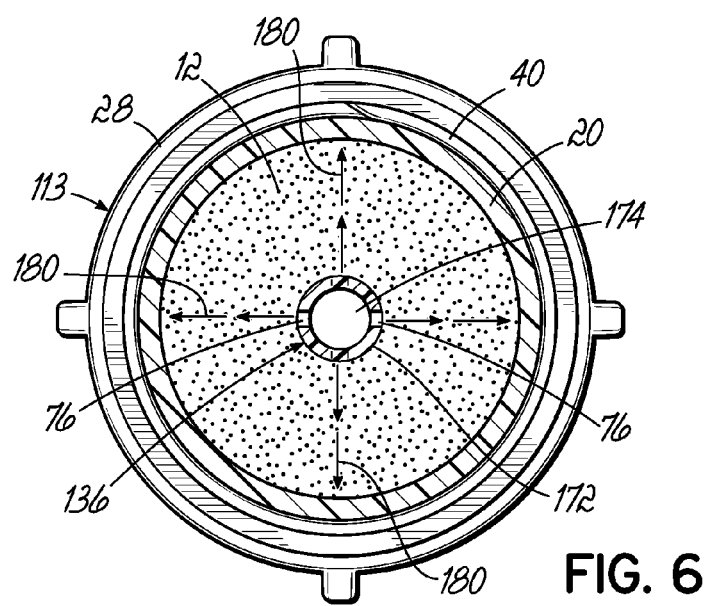
FIG. 6 is a cross-sectional view taken along section line 6-6 of FIG. 5.
Figure 7:
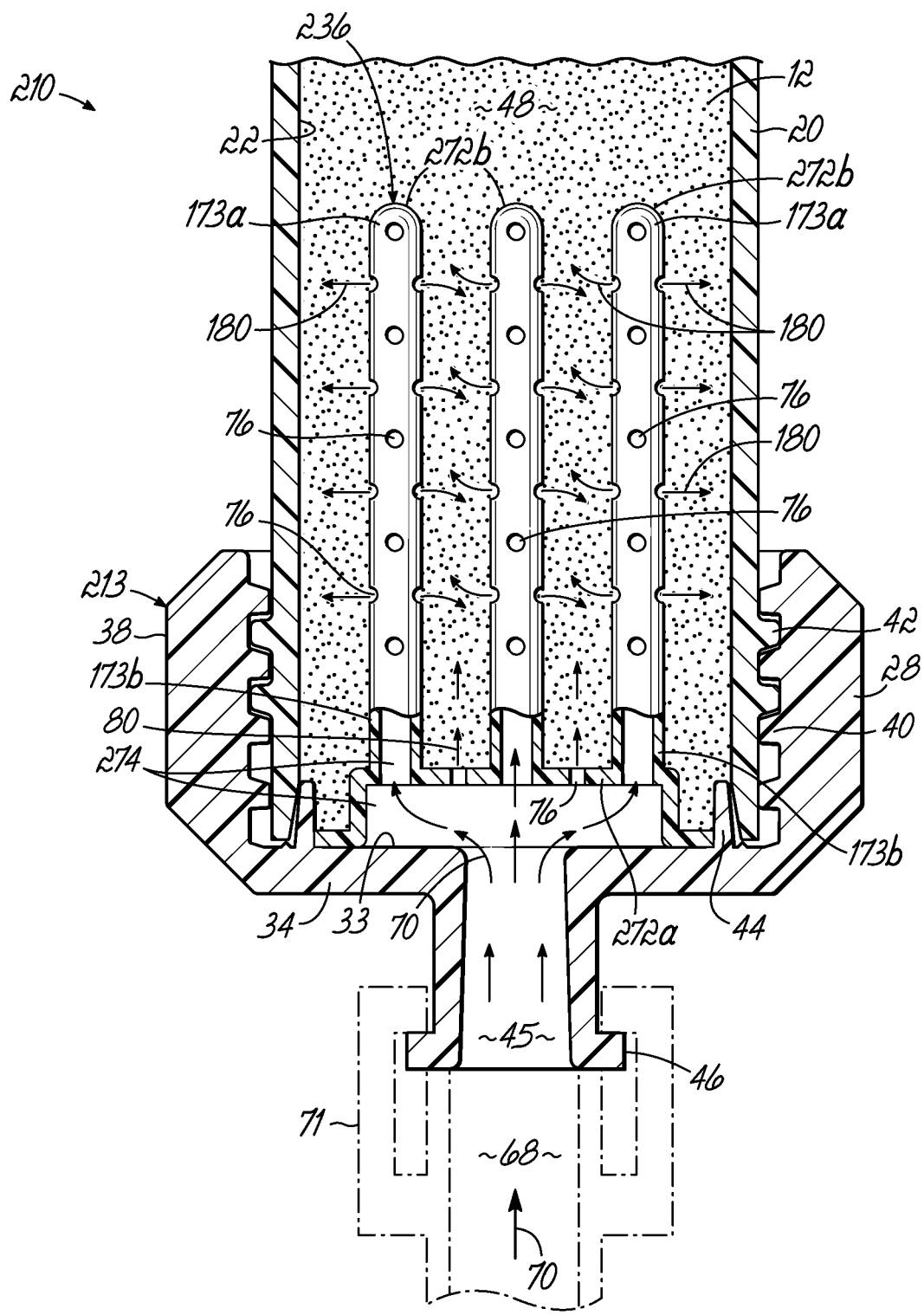
FIG. 7 is an enlarged cross-sectional view similar to FIG. 3, but showing a third embodiment of a device having a diffuser with a wall including a baffle plate and a plurality of cannulae.

One of ordinary skill in the art will readily appreciate that other embodiments of the wall 36 may vary in shape for diffusing and distributing the liquid component 14 throughout the particulate component 12 in order to improve hydration as discussed above. By way of example, FIGS. 5-7 show a second embodiment of a device 110 having a diffuser 113 and a third embodiment of a device 210 having a diffuser 213 for use with the syringe 18 and end cap 28 that similarly distributes the liquid component 14 throughout the particulate component 12. In this respect, like numbers shown in FIGS. 5-7 indicate like features described above. Given the similarities between the exemplary embodiments of the first, second and third devices 10, 110, 210, the distribution of the liquid component 14 will be collectively described below following the description of second and third embodiments of the devices 110, 210.

With respect to FIG. 5 and FIG. 6, the second embodiment of the device 110 has the diffuser 113. The diffuser 113 includes a wall 136 having a cannula or tube 172 with a proximal closed end portion 173a and a distal open end portion 173b. The cannula 172 is generally tubular and projects proximally from the distal plate 34. The distal open end portion 173b mechanically and fluidly connects to the distal plate 34 by insertion into the inlet 45 for receiving the liquid component 14 from the inlet 45. In this respect, a circumference of the cannula 172 is generally similar in size to a circumference of the inlet 45. According to an exemplary embodiment, the wall 136 is of unitary construction.

The cannula 172 defines a volume 174 in fluid communication with the inlet 45. In this respect, the wall 136 maintains the volume 174 between the inlet 45 and the particulate component 12. Furthermore, the plurality of orifices 76 extend in a generally transverse direction through the cannula 172 for fluidly connecting the volume 174 to the chamber 48. The plurality of orifices 76 operatively diffuse the liquid component 14 and allow the liquid component 14 to pass through the cannula 172.

According to an exemplary embodiment of the cannula 172, the plurality of orifices 76 are arranged along the longitudinal direction of the cannula 172 in generally linear rows. More particularly, the cannula 172 includes four linear rows of orifices 76 in which two opposing rows include four orifices each and two other opposing rows include three orifices each. Furthermore, each row of orifices 76 is offset from the adjacent row such that each orifice 76 extends in generally transverse directions about the cannula 172 and toward the syringe body 20 as shown in FIG. 5 and FIG. 6. As such, an exemplary embodiment of the cannula 172 includes fourteen orifices 76 that are generally evenly distributed about the cannula 172 and extend in generally four transverse directions that are also generally orthogonal to the inlet 45. However, it will be appreciated that any number of orifices 76 may be similarly used and vary in shape and size.

As such, the cannula 172 is not intended to be limited to the exemplary embodiments described herein.

Furthermore, each of the orifices 76 has an individual cross-sectional area through which the liquid component may flow from the volume 174 to the chamber 48. In order to encourage a generally equal flow 70 of the liquid component 14 through each of the orifices 76, the cumulative cross-sectional area of the plurality of orifices is sized such that the cannula 172 generates the back pressure against the flow 70 of liquid component 14 as described above. However, it will be appreciated that the diffuser 113 may alternatively diffuse the liquid component 14 without the presence of back pressure. Thus, the invention described herein is not intended to be necessarily limited to include the plurality of orifices 76 with the cumulative cross-sectional area less than the inlet cross-sectional area.

With respect to FIG. 7, the third embodiment of the device 210 has the diffuser 213. The diffuser 213 includes a wall 236 having a baffle plate 272a and a plurality of cannulae or tubes 272b. Generally, the baffle plate 272a and each cannula 272b are similar to the baffle plate 72 and cannula 172 described above. However, rather than the distal open end portion 173b of the cannula 172 connecting to the distal plate 34 as shown in FIG. 7, the baffle plate 272a connects to the distal plate 34 and the distal open end portion 173b connects to the baffle plate 72 for fluid communication with the inlet 45. Thus, the baffle plate 272a and the plurality of cannulae 272b define a volume 274 in fluid communication with the inlet 45. As described above, the wall 236 maintains the volume 274 between the inlet 45 and the particulate component 12. While an exemplary embodiment of the diffuser 213 includes one generally central cannula 272b with a pair of surrounding cannulae 272b, it will be appreciated that any number of cannulae may be positioned about the baffle plate 272a. For example, the diffuser 213 may alternatively include only one generally central cannula 272b projecting from the baffle plate 272a. Furthermore, according to an exemplary embodiment, the wall 236 is of unitary construction.

A plurality of orifices 76 extend through the wall 236 in both generally transverse and longitudinal directions as described above for diffusing the liquid component 14. A portion of the plurality of orifices 76 are generally evenly distributed about the plurality of cannulae 272b in the transverse direction, whereas the remaining portion of the plurality of orifices 76 are generally evenly distributed about the baffle plate 272a between each of the cannulae 272b. As described above, it will be further appreciated that any number of orifices 76 may be used and may vary in shape and size for diffusing the liquid component 14. Furthermore, the baffle plate 272a, each cannula 272b, and the plurality of orifices 76 may used in any combination for forming one or more varieties of diffusers that may accommodate various back pressures related to any type of particulate and liquid biomaterial components for use therein.

In use, the liquid component 14 hydrates the particulate component 12 as shown in FIG. 2 and FIG. 3. The practitioner fluidly connects the primary channel 68 to the inlet 45 by mechanically coupling the male luer coupling 46 to the female luer coupling 71. Once coupled, the chamber 48 containing the particulate component 12 fluidly connects to the first and second syringe chambers 54, 56 containing the first and second liquid bone graft materials 19a, 19b. The practitioner compresses the first and second syringe chambers 54, 56 to generate a positive pressure therein. The positive pressure forces the first and second liquid bone graft materials 19a, 19b simultaneously toward the particulate component 12, as respectively indicated by arrows 69a, 69b. As the first and second liquid bone graft materials 19a, 19b are forced toward the chamber 44, the chamber 44 may vent gas proximally through the filter media 32a, as described above. In this way, the filter media 32a inhibits backpressure from collecting within the chamber 44.

The first and second liquid bone graft materials 19a, 19b combine in the primary channel 68 to form the liquid component 14 flowing into the inlet 45, which is indicated by arrows 70. As such, the liquid component 14 fluidly communicates through the inlet 45 and flows into the volume 74. The pressure forces the liquid component 14 toward and through the wall 36 via the plurality of orifices 76. The plurality of orifices 76 divides the flow 70 of the liquid component 14 passing therethrough to effectively diffuse the flow of the liquid component 14, as indicated by arrows 80. The diffused flows 80 of liquid component 14 are then introduced into the particulate component 12 at each of the orifices 76. The liquid component 14 distributes throughout the particulate component 12 under the influence of the pressure, capillary attraction, and wicking once received in the chamber 48. The liquid component 14 continues to distribute throughout the particulate component 12 until the particulate component 12 is effectively hydrated by the liquid component 14.

With respect to first embodiment of the diffuser 13 including the baffle plate 72, the plurality of orifices 76 extend generally longitudinally through the baffle plate 72. As such, the pressure directs the flow 70 through baffle plate 72, which, in turn, directs each diffused flow 80 of the liquid component 14 into the particulate component 12 in the generally longitudinal direction. Given the form of the baffle plate 72, the stopper end 32 of the plunger 16 nearly extends to the distal opening 26 of the syringe body 20. Thus, the chamber 48 may accommodate a volume of particulate component 12 from approximately zero to approximately a volume of the cavity 22. However, a maximum distance the liquid component 14 flows is distally through an entire longitudinal depth of the particulate component 12 in order to hydrate the particulate component 12.

With respect to the second embodiment of the diffuser 113 including the cannula 172 shown in FIG. 5 and FIG. 6, the plurality of orifices 76 extend generally transversely through the cannula 172. As such, the pressure directs the flow 70 through the cannula 172, which, in turn, directs each diffused flow 180 of the liquid component 14 into the particulate component 12 in the generally transverse direction. Given the form of the cannula 172, the stopper end 32 of the plunger 16 extends only as far as the proximal closed end portion 173a of the cannula 172. Thus, the chamber 48 requires a minimum depth of particulate that extends distally from the inner face 33 of the distal plate 34 to at least the proximal closed end portion 173a. However, a maximum distance the liquid component 14 flows is transversely from the cannula 172 to the syringe body 20. Unless the particulate component 12 is relatively shallow, the transverse distance from the cannula 172 to the syringe body 20 is less than entire depth of the particulate component 12.

With respect to the third embodiment of the diffuser 213, the baffle plate 272a and the cannulae 272b shown in FIG. 7 operate generally as described above with respect to the baffle plate 72 and the cannula 172 shown in FIG. 3 and FIG. 5. While cannulae 272b may prevent the stopper end 32 from moving distally to the baffle plate 272a, the combined baffle plate 272a and cannulae 272b provide for the plurality of orifices 76 to extend in both generally longitudinal and generally transverse directions. Specifically, some of the plurality of orifices 76 direct diffused flow 80 of the liquid component 14 into the particulate component 12 in the generally longitudinal direction (i.e., those orifices 76 in the baffle plate 272a. The remaining portion of the plurality of orifices 76 direct the diffused flow 180 of the liquid component 14 into the particulate component 12 in the generally transverse direction.

According to an exemplary embodiment, compression of the first and second syringe chambers 54, 56 generates the positive pressure that acts upon the first and second liquid bone graft materials 19a, 19b and, ultimately, hydrates the particulate component 12 with the liquid component 14 as described above. However, it will be appreciated that other mechanisms may be used for moving the flow 70 of the liquid component 14 into the cavity 22 for introduction into the particulate component 12. More particularly, it will be further appreciated that the mechanisms may generate the positive pressure as described above and/or a vacuum for moving the flow 70 of the liquid component 14. For example, the stopper end 32 may be configured to contain a vacuum within the chamber 48 in an exemplary embodiment. As such, the operator may withdraw the plunger 16 from the cavity 22 to expand the chamber 48 and, in turn, generate the vacuum that draws upon the first and second liquid bone graft materials 19a, 19b. While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. A device for improving hydration of a particulate component of biomaterial with a liquid component of biomaterial, the device comprising:
    a syringe having a syringe body and a cavity therein for containing the particulate component, the syringe body including a distal opening;
    a distal plate removably connected to the syringe body and at least partially covering the distal opening, the distal plate having an inlet extending therethrough for receiving the liquid component;
    a wall connected to the distal plate and positioned within the cavity, the wall at least partially defining a volume in fluid communication with the inlet, and the wall being configured to maintain the volume between the inlet and the particulate component within the cavity of the syringe; and
    at least one orifice extending through the wall and fluidly connecting the volume to the cavity such that the liquid component received by the inlet flows throughout the volume and into the cavity via the at least one orifice for diffusion of the liquid component and hydration of the particulate component within the cavity of the syringe,
    wherein a cross-sectional area of the at least one orifice is less than a cross-sectional area of the inlet.

2. The device of claim 1 wherein the at least one orifice includes a plurality of orifices for diffusing the liquid component and hydrating the particulate component.

3. The device of claim 2 wherein each of the plurality of orifices is generally circular in shape and the orifices are distributed generally evenly throughout the wall.

4. The device of claim 1 wherein at least a portion of the distal plate forms an end cap, and the end cap is removably attached to the syringe body and covering the distal opening.

5. The device of claim 1 wherein at least a portion of the wall forms a baffle plate.

6. The device of claim 1 wherein at least a portion of the wall forms a cannula.

7. The device of claim 1 wherein a portion of the wall forms a baffle plate and another portion of the wall forms at least one cannula.

8. The device of claim 1, wherein the wall is fixed to the distal plate.

9. A diffuser for improving hydration of a particulate component of biomaterial with a liquid component of biomaterial, the particulate component contained within a cavity of a syringe, the diffuser comprising:
    a distal plate configured for removable attachment to the syringe, the distal plate having an inlet extending therethrough for receiving the liquid component;
    a wall connected to the distal plate and configured to be positioned within the cavity, the wall at least partially defining a volume in fluid communication with the inlet, and the wall being configured to maintain the volume between the inlet and the particulate component within the cavity of the syringe; and
    at least one orifice extending through the wall and configured to be in fluid communication with the volume such that the liquid component received by the inlet is configured to flow throughout the volume and through the orifice for diffusion of the liquid component and hydration of the particulate component within the cavity of the syringe,
    wherein a cross-sectional area of the at least one orifice is less than a cross-sectional area of the inlet.

10. The diffuser of claim 9 wherein the at least one orifice includes a plurality of orifices for diffusing the liquid component and hydrating the particulate component.

11. The diffuser of claim 10 wherein each of the plurality of orifices is generally circular in shape and the orifices are distributed generally evenly throughout the wall.

12. The diffuser of claim 9 wherein at least a portion of the distal plate forms an end cap, and the end cap is configured to removably attach to the syringe.

13. The diffuser of claim 9 wherein at least a portion of the wall forms a baffle plate.

14. The diffuser of claim 9 wherein at least a portion of the wall forms a cannula.

15. The diffuser of claim 9 wherein a portion of the wall forms a baffle plate and another portion of the wall forms at least one cannula.

16. The diffuser of claim 9, wherein the wall is fixed to the distal plate.

17. A method of improving hydration of a particulate component of biomaterial with a liquid component of biomaterial, the particulate component contained within a syringe and positioned against a wall having at least one orifice extending therethrough, the wall being connected to a distal plate having an inlet, the distal plate being removably connected to the syringe, the method comprising:
    diffusing a flow of the liquid component through the inlet of the distal plate and the at least one orifice in the wall in order to form at least one diffused flow of liquid component;

introducing the diffused flow of the liquid component into the particulate component within the syringe; and distributing the liquid component throughout the particulate component in order to hydrate the particulate component with the liquid component.

18. The method of claim 17 wherein at least a portion of the wall forms a baffle plate, the method further comprising:

directing the flow through the baffle plate.

19. The method of claim 18 wherein the at least one orifice extends in a generally longitudinal direction, the method further comprising:

directing the diffused flow of the liquid component into the particulate component in the generally longitudinal direction within the syringe.

20. The method of claim 17 wherein at least a portion of the wall forms at least one cannula, the method further comprising:

directing the flow through the at least one cannula.

21. The method of claim 20 wherein the at least one orifice extends in a generally transverse direction, the method further comprising:

directing the diffused flow of the liquid component into the particulate component in the generally transverse direction.

22. The method of claim 17 wherein a portion of the wall forms a baffle plate and another portion of the wall forms at least one cannula, and diffusing the flow further comprises:

directing the liquid component through the baffle plate and through the at least one cannula.

23. The method of claim 22 wherein at least one orifice extends in a generally longitudinal direction and at least one other orifice extends in a generally transverse direction, the method further comprising:

directing at least one diffused flow of the liquid component into the particulate component in the generally longitudinal direction; and directing at least one other diffused flow of the liquid component into the particulate component in the generally transverse direction.

24. The method of claim 17 wherein the at least one orifice includes a plurality of orifices, the method further comprising:

dividing the flow of the liquid component through the plurality of orifices to create a plurality of diffused flows of liquid component.

25. The method of claim 17 wherein the wall is operatively connected to an end cap having an inlet, the method further comprising:

fluidly coupling a source of the liquid component to the end cap; and fluidly communicating the liquid component through the inlet and toward the wall.

26. The method of claim 17, wherein a volume is at least partially between the wall and an inlet, the method further comprising:

introducing a first liquid material and a second liquid material into the volume; and mixing the first liquid material and the second liquid material within the volume to form the liquid component.

27. The method of claim 17, wherein the wall is fixed to the distal plate.

* * * * *